United States Patent [19]

Hauske

[11] 4,363,803
[45] Dec. 14, 1982

[54] 3",4"-OXYALLYLENE ERYTHROMYCIN AND OLEANDOMYCIN, COMPOSITION AND METHOD OF USE

[75] Inventor: James R. Hauske, East Lyme, Conn.

[73] Assignee: Pfizer Inc.

[21] Appl. No.: 354,124

[22] Filed: Mar. 1, 1982

[51] Int. Cl.³ .................. A61K 31/71; C07H 17/08
[52] U.S. Cl. ................................ 424/180; 536/7.2
[58] Field of Search ............. 424/180, 181; 536/9, 536/17 R

[56] References Cited

U.S. PATENT DOCUMENTS 2,653,899  9/1953  Bunch et al. ..................... 167/65
3,022,219  2/1962  Celmer ............................ 167/65
3,417,077 12/1968  Murphy et al. ................. 260/210
4,069,379  1/1978  Sciavolino ....................... 536/9
4,125,705 11/1978  Sciavolino ....................... 536/9
4,150,220  4/1979  Sciavolino ....................... 536/9

OTHER PUBLICATIONS

K. Gerzon, et al., J. Am. Chem. Soc., 78, 6396 (1956).
M. V. Sigal, et al., J. Am. Chem. Soc., 78, 388 (1956).

Primary Examiner—Johnnie R. Brown
Attorney, Agent, or Firm—Charles J. Knuth; Albert E. Frost; James M. McManus

[57] ABSTRACT

The reaction product of dimethyl diazomethylphosphonate with 4"-deoxy-4"-oxo-oleandomycin and erythromycin A derivatives as antibacterial agents.

17 Claims, No Drawings

3",4"-OXYALLYLENE ERYTHROMYCIN AND OLEANDOMYCIN, COMPOSITION AND METHOD OF USE

FIELD OF THE INVENTION

This invention relates to novel semi-synthetic macrolide antibiotics and in particular to congeners of erythromycin and oleandomycin having antibacterial activity.

DESCRIPTION OF THE ART

Oleandomycin, its production in fermentation broths and its use as an antibacterial agent were first described in U.S. Pat. No. 2,757,123. The naturally occurring compound is known to have the following structure:

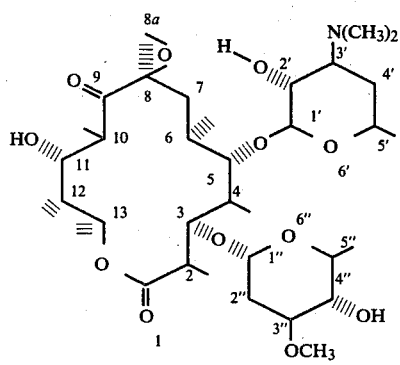

The conventionally accepted numbering scheme and stereochemical representation for oleandomycin and similar compounds is shown at a variety of positions.

Several synthetic modifications of this compound are known, particularly those in which from one to three of the free hydroxyl groups found at the 2', 4" and 11-positions are esterified as acetyl esters. In addition, there are described in U.S. Pat. No. 3,022,219 similar modifications in which the acetyl in the abovementioned esters is replaced with another, preferably unbranched lower alkanoyl of three to six carbon atoms. U.S. Pat. No. 4,125,705 described the preparation of a series of 4"-oxo-oleandomycin derivatives as useful intermediates leading to antibacterial agents.

Erythromycin is an antibiotic formed during the culturing of a strain of *Streptomyces erythreus* in a suitable medium as taught in U.S. Pat. No. 2,653,899. Erythromycin, which is produced in two forms, A and B, is represented by the following structure:

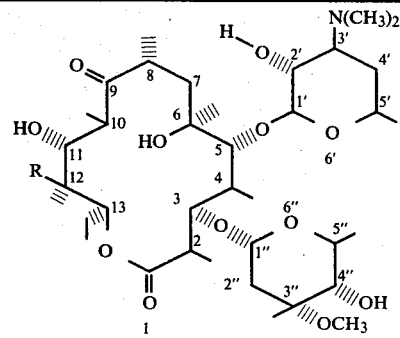

| Erythromycin | R |
|---|---|
| A | —OH |
| B | —H |

Numerous derivatives of erythromycin have been prepared in an effort to modify its biological or pharmacodynamic properties.

U.S. Pat. No. 3,417,077 describes the reaction product of erythromycin and ethylene carbonate as a very active antibacterial agent. U.S. Pat. No. 3,884,903 discloses 4"-deoxy-4"-oxo-erythromycin A and B derivatives as being useful as antibiotics, and U.S. Pat. No. 4,150,220 describes a new synthesis for 4"-oxo-erythromycin and its use as an intermediate leading to antibacterial agents. 9-Dihydroerythromycin A was reported by K. Gerzon, et. al., *J. Am. Chem. Soc.*, 78, 6396 (1956) and M. V. Sigal, et. al., *J. Am. Chem. Soc.*, 78, 388 (1956).

SUMMARY OF THE INVENTION

The semisynthetic macrolide antibacterial agents of this invention are represented by the formulae:

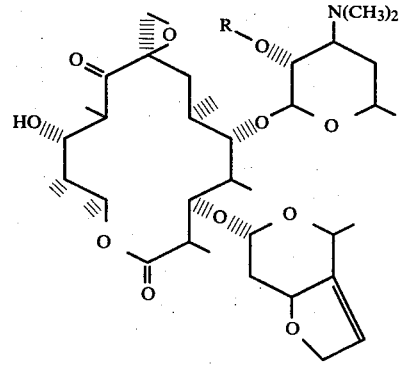

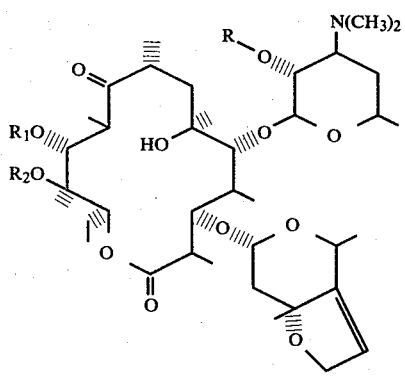

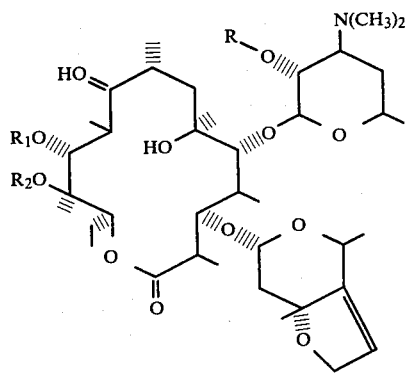

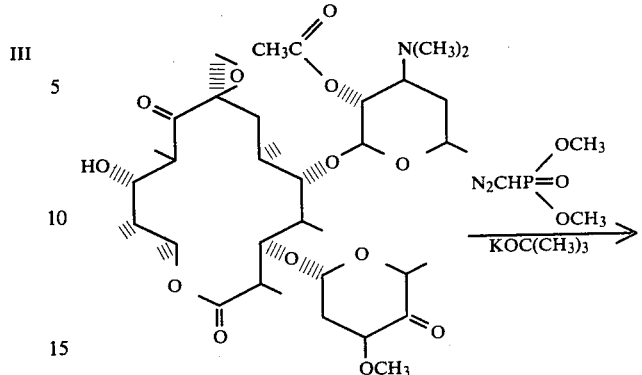

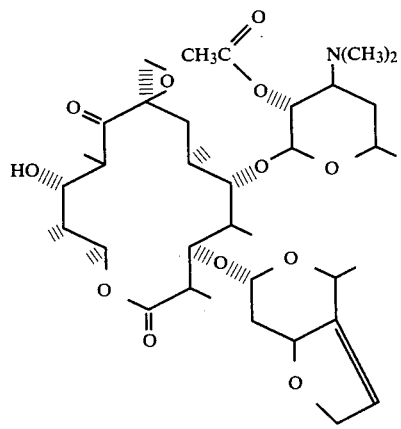

and the pharmaceutically acceptable acid addition salts, wherein R is hydrogen or alkanoyl of two to three carbon atoms; $R_1$ and $R_2$ when taken separately are each hydrogen; and $R_1$ and $R_2$ when taken together are $(CH_3)_2C$.

A preferred group of compounds are those of formula I. Especially preferred within this group is the compound wherein R is acetyl or hydrogen.

A second group of preferred compounds are those of formula II, wherein R is hydrogen or acetyl. Especially preferred within this group is the compound wherein $R_1$ and $R_2$ are each hydrogen.

A third group of preferred compounds are those of formula III, wherein R is hydrogen or acetyl. Especially preferred within this group are the compounds wherein $R_1$ and $R_2$ are each hydrogen and wherein $R_1$ and $R_2$ when taken together are $(CH_3)_2C$.

Also part of this invention is a pharmaceutical composition suitable for oral administration composed of a pharmaceutically acceptable carrier and a therapeutically-effective amount of an antibacterial agent where said agent is of formula I, II or III wherein R, $R_1$, and $R_2$ are as defined.

The formal nomenclature used in naming the erythromycin A and oleandomycin antibacterial agents of this invention is complex. The erythromucin A congener would be named 3-O-de(2,6-dideoxy-3-C-methyl-3-O-methyl-α-L-ribo-hexopyransyl-3-O-([4,7a-dimethyl-4,6,7,7a-tetrahydro-2H-furo{3,2-b}pyran]-6-yl) erythromycin A. In order to further simplify the naming of these compounds, the following name, as applied to erythromycin A, has been employed hereinafter: 3"-demethoxy-4"-deoxy-3",4"-oxyallylene-erythromycin A.

DETAILED DESCRIPTION OF THE INVENTION

In accordance with the process employed for synthesizing the antibacterial agents of the present invention, the following scheme, starting with 2'-acetyl 4"-deoxy-4"-oxo-oleandomycin, is illustrative:

The above described scheme is equally applicable to the preparation of compounds I, II and III, wherein R, $R_1$ and $R_2$ are as previously defined, through the reaction of dimethyl diazomethylphosphonate with the appropriate 4"-deoxy-4"-oxo-oleandomycin or erythromycin A derivative.

In practice a reaction-inert solvent containing the requisite 4"-deoxy-4"-oxo-oleandomycin or erythromycin A and dimethyl diazomethylphosphonate is treated with a slurry or solution of potassium t-butoxide in a reaction-inert solvent.

Although one mole of the 4"-deoxy-4"-oxo-oleandomycin or erythromycin A derivative reacts with one mole of the diazophosphonate, it is preferred that a fifty percent excess of the latter reagent be employed in order to enhance the yield of product. Regarding the amount of base potassium t-butoxide, it is required that as much as three and a half moles per mole of macrolide be employed.

As previously indicated, the base is added to a solution of the macrolide and diazophosphonate. Since the addition of base to these reagents is strongly exothermic, it is necessary to cool the reaction mixture to 0°–5° C. and maintain these temperatures by continued cooling and slow addition of the requisite base. Under these reaction temperature conditions, 0°–5° C., the reaction is complete usually within 10–15 minutes.

Potassium t-butoxide is the base used for the process of this invention. In addition, other bases can be used with similar results; these include alkyl lithiums, such as butyl lithium, alkali metal hydrides, such as sodium and potassium hydrides, and alkali metal alkoxides, such as sodium ethoxide.

As for the solvent in which the aforedescribed process can be conducted, a reaction-inert solvent is preferred. By such a solvent is meant one which solubilizes the appropriate reagents but does not react to any appreciable extent with either the starting reagents or final product. Solvents or mixtures thereof which are suitable include ethers, such as diethyl ether, tetrahydrofuran and dioxane, alkanols, such as isopropanol amd methanol, alkyl acetates such as ethyl acetate and aromatic hydrocarbons such as toluene.

On completion of the reaction the mixture is poured into water and a water immiscible solvent, such as ethyl acetate, and the product isolated from the organic layer. Purification of the product is achieved by simple recrystallization or by column chromatography.

Synthesis of compounds of formulae I-III wherein R is hydrogen can be carried out by the solvolysis of said compound wherein R is alkanoyl as defined. The preferred solvent for this conversion is methanol. In practice a solution of the appropriate compound of formulae I-III wherein R is alkanoyl as defined is heated in methanol at the reflux temperature for 6–12 hours. The solvent is then removed and the residue product purified by partitioning between methylene chloride and water at pH 9. The product, present in the organic phase of the mixture, is obtained by removal of the separated methylene chloride layer.

The reagents for the process leading to the compounds of the present invention are all known in the art, are commercially available or are described herein. The preparation of the 4''-deoxy-4''-oxo-oleandomycins and erythromycins are reported in U.S. Pat. No. 4,125,705 and 4,150,220. Dimethyl diazomethylphosphonate is synthesized according to the method of D. Seyferth, et al., Tetrahedron Lett., 2493 (1970).

Preferred among these compounds because of their antibacterial utility are 2'-acetyl-3''-demethoxy-4''-deoxy-3'',4''-oxyallylene-oleandomycin, 2'-acetyl-3''-demethoxy-4''-deoxy-3'',4''-oxyallylene-erythromycin A, 9-dihydro-2'-acetyl-3''-demethoxy-4''-deoxy-3'',4''-oxyallylene-erythromycin A, 9-dihydro-11,12-O-isopropylidene-2'-acetyl-3''-demethoxy-4''-deoxy-3'',4''-oxyallylene-erythromycin A, 3''-demethoxy-4''-deoxy-3'',4''-oxyallylene oleandomycin, 3''-demethoxy-4''-deoxy-3'',4''-oxyallylene erythromycin A, 9-dihydro-3''-demethoxy-4''-deoxy-3'',4''-oxyallylene erythromycin A and 9-dihydro-11,12-O-isopropylidene-3''-demethoxy-4''-deoxy-3'',4''-oxyallylene-erythromycin A.

In the utilization of the chemotherapeutic activity of those compounds of the present invention which form salts, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic, gluconic and aspartic acids.

The novel oleandomycins and erythromycins described herein exhibit in vitro activity against a variety of Gram-positive microorganisms such as *Staphylococcus aureus* and *Streptococcus pyogenes* and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sick-room utensils; and as industrial antimicrobials, for example, in water treatment, slime control, paint and wood preservation.

For *in vitro* use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive and certain Gram-negative microorganisms in vivo such as *Pasteurella multocida* and *Neisseria sicca* via the oral and/or parenteral routes of administration in animals, including man. Their in vivo activity is more limited as regards susceptible organisms and is determined by the usual procedure which comprises treating mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour postinoculation, and is repeated 4, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 100 mg/kg to about 200 mg/kg of body weight per day. The favored dosage range is from about 150 mg/kg to about 200 mg/kg of body weight per day. Vehicles suitable for parenteral injection may be either aqueous such as water, isotonic saline, isotonic dextrose, Ringers' solution, or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The following examples are provided solely for the purpose of illustration and are not to be construed as limitations of this invention, many variations of which are possible without departing from the spirit or scope thereof.

EXAMPLE 1

2'-Acetyl-3''-demethoxy-4''-deoxy-3'',4''-oxyallylene-erythromycin A (II; $R=CH_3CO$, $R_1$ and $R_2=H$)

To a solution of 10 g (12.9 mmoles) of 2'-acetyl-4''-deoxy-4''-oxo-erythromycin A in 50 ml of tetrahydrofuran cooled to 0°–5° C. in a dry three-necked flask under a nitrogen atmosphere was added 2.91 g (19.4 mmoles) of dimethyl diazomethylphosphonate in 20 ml of tetrahydrofuran at 0° C. To the resulting reaction mixture was then added 5.1 g (45.3 mmoles) of potassium t-butoxide in 50 ml of the same solvent at such a rate that the temperature was maintained at 5°–10° C. After allowing the reaction mixture to stir for 10 minutes, it was poured into 700 ml of ethyl acetate and 1 liter of water. The organic phase was separated, washed successively with water and a saturated brine solution and dried over sodium sulfate. Removal of the solvent in vacuo gave 8.1 g (81% yield) of the desired product, m.p. 125°–127° C.

The NMR spectrum (CDCl$_3$) showed absorption at 0.8–1.4 (39H, m) 2.1 (3H, s), 2.3 (6H, s) and 3.3–5.5 (19H, m) ppm.

Starting with 2'-propionyl-4''-deoxy-4''-oxo-erythromycin A and following the above procedure 2'-propionyl-3''-demethoxy-4''-deoxy-3'',4''-oxyallylene-erythromycin A (II; $R=CH_3CH_2CO$, $R_1$ and $R_2=H$) is prepared.

EXAMPLE 2

11,12-O-Isopropylidene-2'-propionyl-3''-demethoxy-4''-deoxy-3'',4''-oxyallylene-erythromycin A (II; $R=CH_3CH_2CO$, $R_1$, $R_2=(CH_3)_2C$)

A solution of 10.7 g (12.9 mmoles) of 11,12-O-isopropylidene-2'-propionyl-4''-deoxy-4''-oxo-erythromycin A in 50 ml of tetrahydrofuran at 0°–5° C. under a nitrogen atmosphere is treated with 2.91 g (19.4 mmoles) of dimethyl diazomethylphosphonate in 25 ml of the same solvent, followed by the addition of 5.1 g (45.3 mmoles) of potassium t-butoxide at such a rate that the temperature of the reaction does not rise above 5° C. After the reaction mixture is allowed to stir in the cold for 15 minutes, it is then added to 750 ml of ethyl acetate and 1 liter of water. The organic layer is separated, washed with water and a brine solution and dried over sodium sulfate. Removal of the solvent under vacuum provides the desired product.

The above procedure is repeated starting with 11,12-O-isopropylidene-2'-acetyl-4''-deoxy-4''-oxo-erythromycin A to give 11,12-O-isopropylidene-2'-acetyl-3''-demethoxy-4''-deoxy-3'',4''-oxyallylene-erythromycin A (II; $R=CH_3CO$, $R_1$, $R_2=(CH_3)_2C$).

EXAMPLE 3

2'-Acetyl-3''-demethoxy-4''-deoxy-3'',4''-oxyallylene-oleandomycin (I; $R=CH_3CO$)

Potassium t-butoxide (43 mg, 0.388 mmoles) in 5 ml of tetrahydrofuran was added slowly to a solution of 100 mg (0.129 mmoles) of 2'-acetyl-4''-deoxy-4''-oxo-oleandomycin and 29 mg (0.194 mmoles) of dimethyl diazomethylphosphonate in 3 ml of tetrahydrofuran at such a rate that the temperature did not go above 0° C. After stirring in the cold (0° C.) for 15 minutes, the reaction mixture was added to 20 ml of ethyl acetate and 20 ml of water. The organic layer was separated, washed with water (1×20 ml) and dried over sodium sulfate. Removal of the solvent gave the desired product as a white foam, 70 mg.

The product was purified by chromatographing on silica gel using chloroform-methanol-concentrated ammonium hydroxide (9:1:0.05; v,v,v) as the eluent.

The NMR spectrum showed absorption at 0.8–1.5 (33H, m), 2.05 (3H, s), 2.3 (6H, s), 2.7 (2H, m) and 3.3–5.4 (15H, m) ppm.

Starting with 2'-propionyl-4''-deoxy-4''-oxo-oleandomycin, and following the above procedure 2'-propionyl-3''-demethoxy-4''-deoxy-3'',4''-oxyallyleneoleandomycin (I; $R=CH_3CH_2CO$) is prepared.

EXAMPLE 4

9-Dihydro-2'-acetyl-3''-demethoxy-4''-deoxy-3'',4''-oxyallylene-erythromycin A (III; $R=CH_3CO$, $R_1$ and $R_2=H$)

To 928 mg (1.2 mmoles) of 9-dihydro-2'-acetyl-4''-deoxy-4''-oxo-erythromycin A in 8 ml of dry tetrahydrofuran under a nitrogen atmosphere and cooled to 0° C. was added 269 mg (1.79 mmoles) of dimethyl diazomethylphosphonate in 4 ml of the same solvent. To this solution was then added over 20 minutes at 0° C. a slurry of 472 mg (4.2 mmoles) of potassium t-butoxide in 12 ml of dry tetrahydrofuran. After 15 minutes the reaction mixture was added to 150 ml of water, 40 ml of ethyl acetate and 10 ml of a saturated salt solution, and the pH adjusted to about 11.5 with 6 N sodium hydroxide solution. The organic phase was separated, washed with water and dried over sodium sulfate. Removal of the solvent gave the desired product as a white foam. Recrystallization from acetone-water gave the purified product, 800 mg, m.p. 132°–133° C.

The NMR spectrum showed absorption at 0.8–1.5 (35H, m), 2.05 (3H, s), 2.30 (6H, s) and 3.4–5.5 (24H, m) ppm.

Following the above procedure and starting with 9-dihydro-2'-propionyl-4''-deoxy-4''-oxo-erythromycin A, 9-dihydro-2'-propionyl-3''-demethoxy-4''-deoxy-3'',4''-oxyallylene-erythromycin A (III; $R=CH_3CH_2CO$, $R_1$ and $R_2=H$) is prepared.

EXAMPLE 5

9-Dihydro-11,12-O-isoproplidene-2'-acetyl-3''-demethoxy-4''-deoxy-3'',4''-oxyallylene-erythromycin A (III; $R=CH_3CO$, $R_1$, $R_2=(CH_3)_2C$)

To 6.63 g (8.12 mmoles) of 9-dihydro-11,12-O-isopropylidene-2'-acetyl-4''-deoxy-4''-oxo-erythromycin A in 12 ml of dry tetrahydrofuran at 0° C. was added 1.82 g (12.18 mmoles) of dimethyl diazomethylphosphonate in 5 ml of the same solvent. To the resulting solution was added 2.76 g (24.6 mmoles) of potassium t-butoxide in 36 ml of tetrahydrofuran at such a rate that the reaction mixture temperature is maintained at 0°-10° C. After stirring in the cold for 10 minutes, the reaction mixture was added to 100 ml of ethyl acetate and 75 ml of water, and the pH adjusted to 11.5 with 6 N sodium hydroxide solution. The organic layer was separated, washed with water and dried over sodium sulfate. Removal of the solvent in vacuo gave 6.05 g of the desired product. Purification was achieved by chromatography on silica gel using acetone-hexane-concentrated ammonium hydroxide (6:4:0.051 v,v,v). The final product was recrystallized from acetone-water, 4.0 g, m.p. 195°-197° C.

The NMR spectrum showed absorption at 0.8-1.5 (35H, m), 1.55 (6H, s), 2.05 (3H, s), 2.30 (6H, s) and 3.4-5.6 (22H, m) ppm.

Starting with 9-dihydro-11,12-O-isopropylidene-2'-propionyl-4"-deoxy-4"-oxo-erythromycin A and following the above procedure 9-dihydro-11,12-O-isopropylidene-2'-propionyl-3"-demethoxy-4"-deoxy-3",4"-oxyallylene-erythromycin A (III; R=CH$_3$CH$_2$CO, R$_1$, R$_2$=(CH$_3$)$_2$C) is prepared.

EXAMPLE 6

3"-Demethoxy-4"-deoxy-3",4"-oxyallylene-erythromycin A (II; R, R$_1$ and R$_2$=H)

A solution of 1.0 g (1.3 mmoles) of 2'-acetyl-3"-demethoxy-4"-deoxy-3",4"-oxyallylene-erythromycin A in 15 ml of methanol was stirred at reflux temperature under nitrogen for 12 hours. The solvent was removed in vacuo and the residual material slurried in 50 ml of methylene chloride and 100 ml of water. The pH of the mixture was adjusted to 9 with dilute aqueous sodium hydroxide and the organic layer separated and dried over sodium sulfate. Removal of the solvent gave 850 mg (90% yield) of the desired product.

The CMR spectrum (CDCl$_3$—off resonance) showed absorption at 221.6, 174.8, 144.0 (s), 118.0 (d), 101.9, 95.8, 85.2, 82.2, 81.6, 76.4, 74.4, 74.2, 72.0, 68.9, 68.4, 68.0, 65.5, 65.3, 45.2, 43.9, 40.0, 38.0, 37.4, 29.4, 29.0, 26.4, 25.4, 21.2, 21.0, 19.6, 18.0, 16.1, 15.3, 15.1, 11.9, 10.4 and 8.9 ppm.

EXAMPLE 7

11,12-O-Isopropylidine-3"-demethoxy-4"-deoxy-3",4"-oxyallylene-erythromycin A (II; R=H, R$_1$,R$_2$=(CH$_3$)$_2$C)

11,12-O-Isopropylidene-2'-acetyl-3"-demethoxy-4"-deoxy-3",4"-oxyallylene-erythromycin A (1.21 g, 1.5 mmoles) is added to 16 ml of methanol and the resulting solution heated at reflux for 10 hours. The methanol is removed under vacuum and the residue partitioned between 50 ml of methylene chloride and 100 ml of water. The pH is adjusted to 9 with 6 N sodium hydroxide solution and the organic phase is separated and dried over sodium sulfate. Removal of the solvent gives the desired product.

EXAMPLE 8

3"-Demethoxy-4"-deoxy-3",4"-oxyallylene-oleandomycin (I; R=H)

A solution of 17 ml of methanol containing 1.14 g (1.5 mmoles) of 2'-acetyl-3"-demethoxy-4"-deoxy-3",4"-oxyallylene-oleandomycin is heated at reflux for 8 hours. The solvent is removed in vacuo, and the residue dissolved in a mixture of 50 ml of methylene chloride and 100 ml of water. Dilute aqueous sodium hydroxide solution is added until the pH is 9, and the organic phase separated and dried over sodium sulfate. Removal of the methylene chloride under vacuum gives the desired product.

EXAMPLE 9

9-Dihydro-3"-demethoxy-4"-deoxy-3",4"-oxyallylene-erythromycin A (III; R, R$_1$ and R$_2$=H)

To 15 ml of methanol is added 1.24 g (1.6 mmoles) of 9-dihydro-2'-acetyl-3"-demethoxy-4"-deoxy-3",4"-oxyallylene-erythromycin A and the resulting solution heated for 8 hours at reflux temperature. The solvent is removed in vacuo and the residue treated with 100 ml of water and 50 ml of methylene chloride. The pH is adjusted to 9 with dilute aqueous sodium hydroxide solution and the organic phase separated and dried over sodium sulfate. The methylene chloride is removed under vacuum to give the desired product.

EXAMPLE 10

9-Dihydro-11,12-O-isopropylidene-3"-demethoxy-4"-deoxy-3",4"-oxyallylene-erythromycin A (III; R=H, R$_1$, R$_2$=(CH$_3$)$_2$C)

To 16 ml of methanol is added 1.13 g (1.4 mmoles) of 9-dihydro-11,12-O-isopropylidene-2'-acetyl-3"-demethoxy-4"-deoxy-3",4"-oxyallylene-erythromycin A and the resulting solution heated to reflux for 12 hours. The solvent is removed in vacuo and the residue dissolved in 50 ml of methylene chloride and 100 ml of water. The pH of the mixture is adjusted to 9 with dilute aqueous sodium hydroxide solution and the organic layer separated and dried over sodium sulfate. Removal of the solvent under vacuum gives the desired product.

PREPARATION A

9-Dihydro-2'-acetyl-4"-deoxy-4"-oxo-erythromycin A (a) 9-dihydro-2'-acetylerythromycin A To 2.0 g of dihydroerythromycin A (M. V. Sigal et al., *J. Am. Chem. Soc.*, 78, 388 (1956) in 8 ml of methylene chloride was added 0.3 ml of acetic anhydride and the resulting reaction mixture allowed to stir under a nitrogen atmosphere for 2 hours. The reaction was added to a mixture of 40 ml of ethyl acetate and 150 ml of water and the pH adjusted to 11.5 with aqueous 6 N sodium hydroxide solution. The organic phase was separated, dried over sodium sulfate and concentrated *in vacuo* to give 1.8 g of the desired intermediate.

In a similar manner, starting with 9-dihydroerythromycin A and propionic anhydride, 9-dihydro-2'-propionylerythromycin A is prepared.

(b) 9-dihydro-2'-acetyl-4"-deoxy-4"-oxo-erythromycin A

To 52 ml of methylene chloride and 4.5 ml of dimethylsulfoxide cooled to −70° C. was added over a period of 7 minutes 8.3 ml of trifluoroacetic anhydride such that the temperature did not exceed −65° C. After stirring 20 minutes at −70° C., 5.3 ml of pyridine was added slowly over a period of 5 minutes, followed, after 5 minutes at −70° C., by the addition over 30 minutes of 16 g of 9-dihydro-2'-acetylerythromycin A in 46 ml of methylene chloride. The reaction mixture was allowed to stir for 30 minutes at −70° C. and was then treated with 21.7 ml of triethylamine at such a rate that the temperature did not exceed −65° C. After stirring for 10 minutes, the reaction mixture was poured into 300 ml of methylene chloride and 800 ml of water and the pH adjusted to 9.5. The organic layer was separated, washed with water and dried over sodium sulfate. Removal of the solvent in vacuo gave 16.1 g of the desired intermediate product. The product can be purified further by recrystallization from acetone-water.

Similarly, starting with 9-dihydro-2'-propionyl-erythromycin A, 9-dihydro-2'-propionyl-4''-deoxy-4''-oxo-erythromycin A is prepared.

PREPARATION B 11,12-O-Isopropylidene-2'-acetyl-4''-deoxy-4''-oxo-erythromycin A (a) 9-dihydro-11,12-O-isopropylidene-2'-acetyl-4''-deoxy-4''-oxo-erythromycin A To 6.0 g of 9-dihydro-2'-acetyl-4''-deoxy-4''-oxo-erythromycin A in 80 ml of methylene chloride cooled to 0° C. was added portionwise 7.3 ml of 2-methoxypropene and 1.33 g of pyridine hydrochloride. The reaction mixture was allowed to warm to room temperature. After stirring overnight, an additional 4 ml of 2-methoxypropane and 30 ml of methylene chloride were added and the mixture allowed to stir for several hours. The mixture was then poured into 80 ml of ethyl acetate and 100 ml of water and the pH adjusted to 11.5 with 6 N sodium hydroxide solution. The organic phase was separated, dried over sodium sulfate and concentrated under vacuum to give 5.6 g of the desired intermediate.

In a similar manner, starting with 9-dihydro-2'-propionyl-4''-deoxy-4''-oxo-erythromycin A, 9-dihydro-11,12-O-isopropylidene-2'-propionyl-4''-deoxy-4''-oxo-erythromycin A is prepared.

(b) 11,12-O-isopropylidene-2'-acetyl-4''-deoxy-4''-oxo-erythromycin A

To 50 ml of methylene chloride and 4.5 ml of dimethylsulfoxide cooled to −70° C. is added over a period of 10 minutes 8.3 ml of trifluoroacetic anhydride at such a rate that the temperature of the cooled reaction mixture does not exceed −65° C. After stirring for 20 minutes at −70° C., 5.3 ml of pyridine is added slowly, followed by the addition of 16.7 g of 9-dihydro-11,12-O-isopropylidene-2'-acetyl-4''-deoxy-4''-oxo-erythromycin A in 45 ml of methylene chloride over a period of 35 minutes. The reaction mixture is allowed to stir at −70° C. for 30 minutes and is then treated with 21.7 ml of triethylamine at such a rate that the temperature does not exceed −65° C. After stirring for 10 minutes, the mixture is poured into 300 ml of methylene chloride and 800 ml of water. The pH is adjusted to 9.5 with aqueous base and the organic layer separated and dried over sodium sulfate. Removal of the solvent in vacuo provides the desired intermediate.

In a similar manner, starting with 9-dihydro-O-11,12-isopropylidene-2'-propionyl-4''-deoxy-4''-oxo-erythromycin A, O-11,12-isopropylidene-2'-propionyl-4''-deoxy-4''-oxo-erythromycin A is produced.

I claim:

1. A compound selected from the group consisting of those of the formulae:

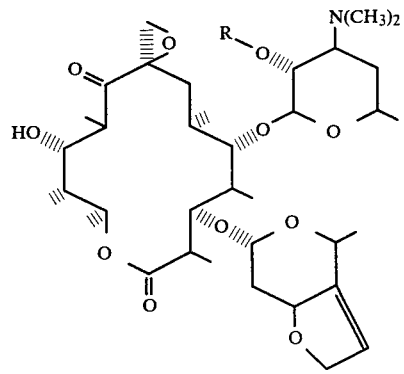

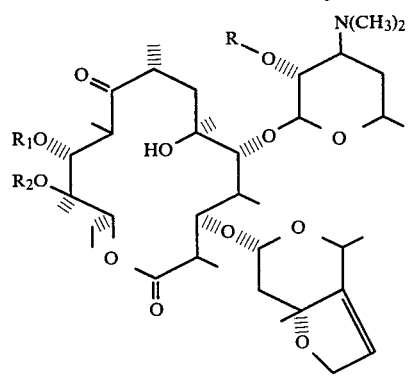

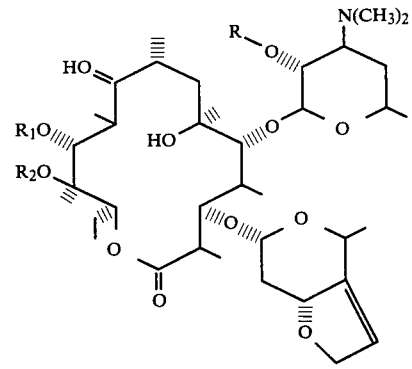

and the pharmaceutically acceptable acid addition salts, wherein R is selected from the group consisting of hydrogen and alkanoyl having two to three carbon atoms; $R_1$ and $R_2$ when taken separately are each hydrogen and $R_1$ and $R_2$ when taken together are $(CH_3)_2C$.

2. A compound of claim 1, formula I.
3. The compound of claim 2, wherein R is acetyl.
4. The compound of claim 2, wherein R is hydrogen.
5. A compound of claim 1, formula II.
6. A compound of claim 5, wherein R is acetyl.
7. The compound of claim 6, wherein $R_1$ and $R_2$ are each hydrogen.
8. A compound of claim 5, wherein R is hydrogen.
9. The compound of claim 8, wherein $R_1$ and $R_2$ are each hydrogen.
10. A compound of claim 1, formula III.
11. A compound of claim 10, wherein R is acetyl.
12. The compound of claim 11, wherein $R_1$ and $R_2$ are each hydrogen.
13. A compound of claim 10, wherein R is hydrogen.
14. The compound of claim 13, wherein $R_1$ and $R_2$ are each hydrogen.
15. The compound of claim 13, wherein $R_1$ and $R_2$ when taken together are $(CH_3)_2C$.
16. The compound of claim 11, wherein $R_1$ and $R_2$ when taken together are $(CH_3)_2C$.
17. A pharmaceutical composition suitable for oral administration comprising a pharmaceutically acceptable carrier and a therapeutically-effective amount of an antibacterial agent wherein said agent is a compound as claimed in claim 1.

* * * * *